United States Patent [19]

Schmitz et al.

[11] Patent Number: 4,717,115
[45] Date of Patent: Jan. 5, 1988

[54] ADJUSTABLE MOLD FOR FABRICATING BONE REPLACEMENTS

[75] Inventors: John P. Schmitz, Columbia; Jeffrey O. Hollinger, Glenwood, both of Md.

[73] Assignee: The United States of America as represented by the Secretary of the Army, Washington, D.C.

[21] Appl. No.: 919,945

[22] Filed: Oct. 14, 1986

[51] Int. Cl.⁴ .................... B29C 33/20; B29C 33/68
[52] U.S. Cl. .................. 249/112; 249/134; 249/141; 249/158; 249/161
[58] Field of Search .............. 249/54, 55, 112, 114, 249/115, 134, 155, 158, 141, 161, 162, 165; 425/812

[56] References Cited

U.S. PATENT DOCUMENTS

| 765,365 | 7/1904 | Lamp'l | 249/105 |
| 864,698 | 8/1907 | Schlock et al. | 249/158 |
| 955,282 | 4/1910 | Pocock | 249/158 |
| 1,323,345 | 12/1919 | Wisner | 249/158 |
| 2,668,999 | 2/1954 | Baechler | 249/158 |
| 3,761,047 | 9/1973 | Mao | 249/115 |
| 3,964,727 | 6/1976 | Gladwin | 249/158 |

FOREIGN PATENT DOCUMENTS

| 2042151 | 3/1972 | Fed. Rep. of Germany | 249/158 |
| 1586203 | 2/1970 | France | 249/115 |

Primary Examiner—Jay H. Woo
Assistant Examiner—James C. Housel
Attorney, Agent, or Firm—Francis A. Cooch

[57] ABSTRACT

The invention is directed to an adjustable mold for use in fabricating biodegradable polymeric bone replacements or implants. The invention consists of a box-like structure with two movable plates therein which can be locked into place permitting different size replacements to be fabricated. The interior walls are panels consisting of polytetrafluoroethylene which permit easy removal of a cured bone replacement. The construction and locking means for the movable plates permit the invention to withstand the pressures developed in replacement fabrication as well as to withstand the most commonly used types of sterilization procedures.

2 Claims, 3 Drawing Figures

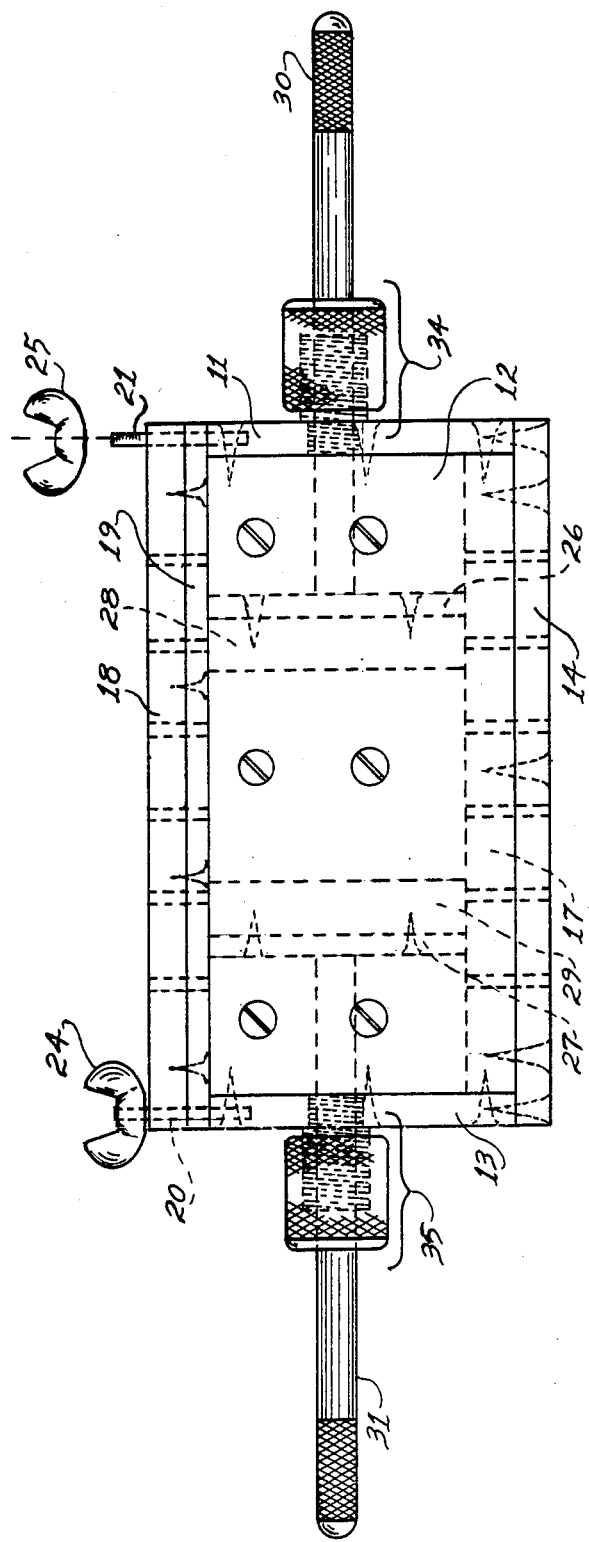

ADJUSTABLE MOLD FOR FABRICATING BONE REPLACEMENTS

BACKGROUND OF THE INVENTION

This invention relates to molds and, more specifically, to an adjustable mold for use in fabricating bone replacements or implants, particularly for the lower jaw (mandible).

For wounds resulting in a tearing away (avulsion) of bony structure, reconstructive surgery, bone implants, and/or grafts are needed to restore bone continuity. Furthermore, the majority of patients who undergo reconstructive facial surgery require partial or complete dentures (dental prostheses). For a dental prosthesis to fit and function properly in the mouth, there must be a successful reconstruction of a bony base ample enough to support the prosthesis.

Current technique for replacing missing mandibular bone involves using a piece of bone taken from another portion of the patient's body. However, replacements for avulsed or excised (resected) segments of the mandibular bone may be possible in the future with synthetic bone implants. Such implants may be made of polymers which are biodegradable, that is, can degrade by biological processes over time as the adjacent bone grows back. As noted above, it is extremely important for successful reconstructive surgery that the geometry of the bone repair material accurately duplicates the lost bone.

Present techniques for fabricating synthetic polymeric bone replacements involve curing them in static, i.e., nonadjustable, mold. However, synthetic bone replacements are needed in many different sizes for use not only in humans but also in laboratory animals since this technology is still primarily experimental. Not only does the use of static molds require that a new mold be constructed each time a new size replacement is required, but, once cured in the mold, replacements frequently stick to the interior surfaces making their removal difficult. Furthermore, these molds, due to their construction, are frequently limited in the methods which can be used to sterilize them.

Adjustable molds do exist, e.g., U.S. Pat. Nos. 3,964,727; 1,323,345; 955,282; and 765,365. However, none exist in the medical field for the purpose of fabricating bone replacements. The cited patents relate to molds for continuous casting of molten steel and for casting concrete and printing type. Obviously, the large size of the molds of the referenced patents, their intended uses, and the lack of ability to sterilize them based on the materials used in their construction would not suggest that they be used or modified to fabricate bone replacements. Furthermore, none of the inventions of the referenced patents employ Applicants' unique design for moving the adjustable portion of the mold and locking it in place.

The use of tetrafluoroethylene polymer in molds also is known. See, e.g., French Patent No. 1,586,203. However, this invention is a static, nonadjustable mold whose ceramic construction would be too brittle to lend itself to bone replacement fabrication.

SUMMARY OF THE INVENTION

The problems described above are solved, to a great extent, through the practice of the invention. Illustratively, a container structure with a removable lid member is constructed of brass, stainless steel, or aluminum. All interior surfaces except two parallel wall members have polytetrafluoroethylene panels attached thereto.

Two plates with polytetrafluoroethylene panels also attached are inserted into the container structure so they can move transversely between, and in contact sealingly with, the two parallel wall members with polytetrafluoroethylene panels attached. These movable plates will also be in contact sealingly with the lid member when in place and the wall member opposite thereto. Attached to each movable plate is a rod which extends rearwardly through the wall member which is parallel to the plate and thereafter through a locking means which is threaded into the hole in the wall member. The locking means permits the rod and, hence, the movable plate to be adjusted and then locked into place.

During operation, the entire mold is first sterilized. Then the movable plates are set the necessary distance apart to create a mold which will produce a properly sized bone replacement or implant for the specific human or animal mandible being reconstructed. Once correctly adjusted, the plates are locked into place, polymer is poured into the mold, and the lid is bolted into place. The air holes in the lid and opposite wall member permit the escape of air and excess polymer. The mold is now set aside for the polymer to cure; this can take place at room temperature or in a vacuum oven. Once cured, the polymer material is removed from the mold, which removal is considerably facilitated by the polytetrafluoroethylene panels.

Thus, the invention provides for a simple, adjustable mold whose construction enables it to withstand sterilization by ethylene oxide gas, steam, or heat and, as well, the pressure developed in the mold by both the compression of the polymer bone material and the expansion thereof as it cures. Most importantly, the size of the mold can vary to permit it to be used for fabricating an almost infinite number of different size bone implants for use in humans and animals. No device currently exists, other than Applicants' invention, which provides these benefits and solves the problems not solved by the prior art.

For a more complete appreciation of the invention, attention is invited to the following detailed description of a preferred embodiment of the invention taken with the figures of the drawings. The scope of the invention, however, is limited only through the claims appended hereto.

BRIEF DESCRIPTION OF THE DRAWINGS

FIG. 2 is a side elevation view of the invention.

DETAILED DESCRIPTION OF THE PREFERRED EMBODIMENT

Figures 1, 3:
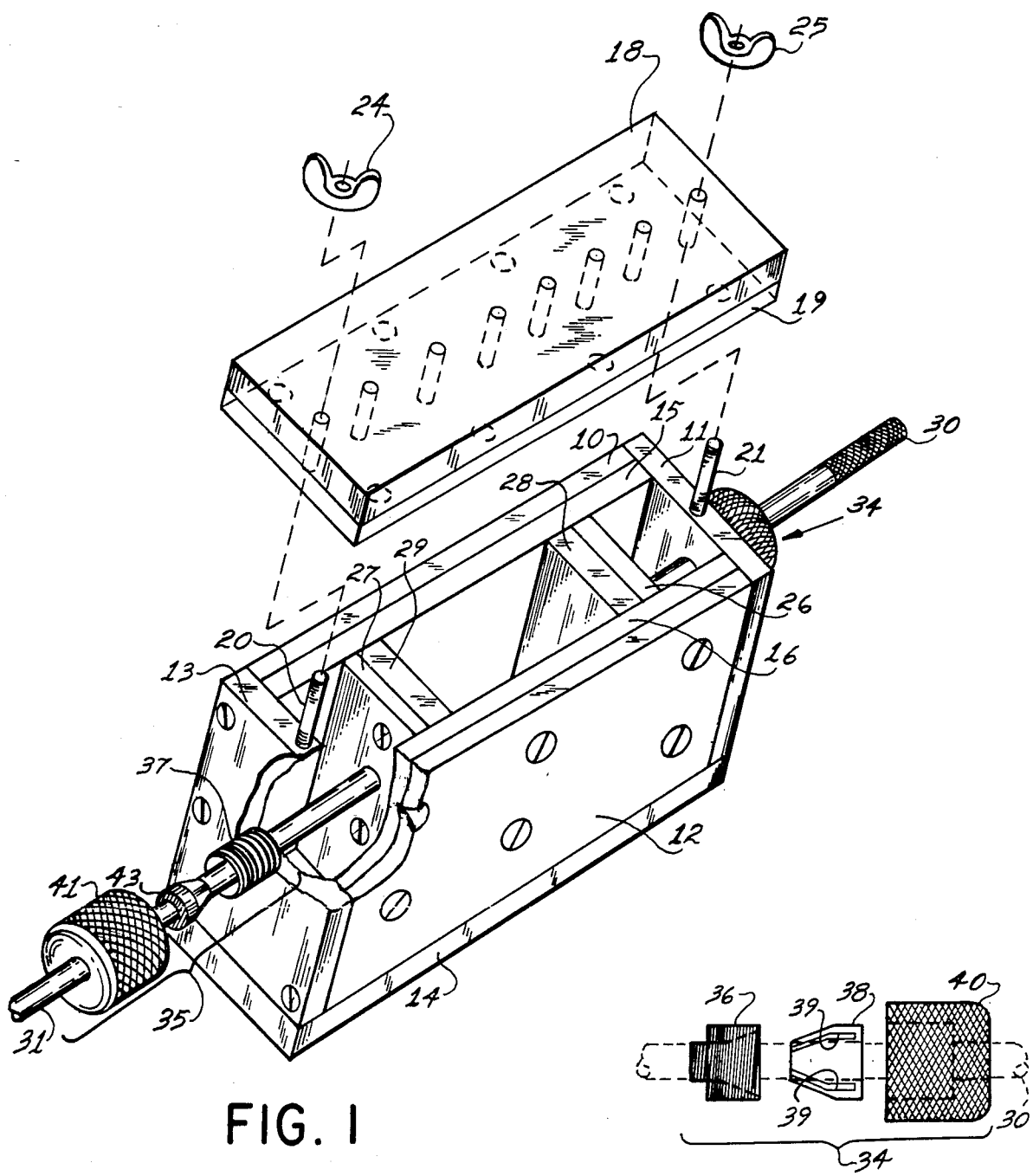
FIG. 1 is a perspective view of a typical embodiment of the invention with part of the mold cut away.
FIG. 3 is a side elevation view of an embodiment of the invention's locking means with the parts disassembled.

An illustrative embodiment of the invention is shown in FIGS. 1 and 2 of the drawings.

In this embodiment five wall members 10, 11, 12, 13, 14 are rigidly attached to each other to form a container structure or mold which is open on one side. The wall members can be made of brass, stainless steel, aluminum or the like. As shown in FIG. 2, wall member 14 opposite the open side has a plurality of through holes.

In a preferred embodiment two parallel wall members, e.g., wall members 10, 12, and wall member 14 opposite the open side, have panels 15, 16, 17, respectively, attached to their interior surface, the panels consisting of a polytetrafluoroethylene polymer or the like. The panels 15, 16, 17 can be attached to the wall members by any one of a number of means. In this case, screws were used. The panel 17 attached to wall member 14, i.e., the wall member opposite the open side, also has a plurality of through holes which are in alignment with the through holes in wall member 14.

A lid member 18, also made of brass, stainless steel, aluminum or the like, with a plurality of through holes and a panel 19 consisting of polytetrafluoroethylene or the like attached with screws or similar means to the interior surface thereof, is adapted to fit sealingly over the open side of the mold formed by the wall members 10, 11, 12, 13, 14. The lid member 18 can be securely fastened over the open side by means of two threaded rods 20, 21 which are secured into the edges of two parallel wall members, 11, 13. The threaded rods 20, 21 fit through two of the through holes in the lid member 18 and the panel 19 attached thereto. Once the lid member 18 is in place over the open side, wing nuts 24, 25 or the like can then be threaded onto the threaded rods 20, 21 to secure the lid member 18 to the mold.

The adjustable feature of the invention in this embodiment is accomplished through the use of two movable plates 26, 27. The plates are fitted into the interior of the mold so that they are parallel to wall members 11, 13, respectively. The edges of each plate 26, 27 are perpendicular to, and fit sealingly against, the wall members 10, 12, 14. Each plate has attached to its interior side a panel 28, 29 consisting of polytetrafluoroethylene or the like. The panels are attached to the plates with screws or the like.

Attached to each plate on the side opposite the panels 28, 29 are rods 30, 31 which are perpendicular to the surface of each plate and which extend rearwardly through holes in wall members 11, 13, respectively. The rods 30, 31 permit the plates 26, 27 to be moved transversely between parallel wall members 10, 12 thereby allowing the user to vary the interior dimensions of the mold from the exterior thereof.

Once the interior dimensions of the mold are the proper size, locking means 34, 35 attached to the exterior side of wall members 11, 13 lock the rods 30, 31 and, hence, the plates 26, 27 in place. Referring to FIG. 3, locking means 34 consists of a hollow threaded member 36, a portion of the length thereof being equal to or slightly less than the thickness of wall member 11 and the circumference of said length matching that of the hole in wall member 11. The hole in wall member 11 is threaded to receive the threaded member 36 the remaining length of which has a circumference which is larger than the hole. This permits threaded member 36 to be threaded tightly into the hole in wall member 11 since the larger circumference portion of the threaded member will abut the exterior surface of wall member 11 surrounding the hole.

The threaded member 36 contains a hole sufficient in size to permit rod 30 to pass there through. As the hole in the threaded member continues away from the mold, however, it widens to become conical in shape. This cone-shaped opening is of a size to receive hollow cone member 38 which fits over the rod 30 and into threaded member 36. The cone member has a plurality of longitudinal openings 39 cut therein which permit the narrow portion of the cone member to be squeezed together thereby decreasing the circumference of the narrower opening thereof.

The final element of the locking means is the nut 40 which fits over the rod 30 and has an interior threaded portion which permits the nut 40 to be threaded onto the larger circumference portion of threaded member 36. The back of the nut 40 has an opening which is smaller than the interior threaded portion thereof but which is big enough to permit rod 30 to slide freely therethrough. Locking means 35 in its construction and operation is a counterpart to locking means 34.

In operation, after sterilization of the entire mold, the plates 26, 27 are moved by means of the rods 30, 31 to create the appropriate size interior dimension for the mold. The nuts 40, 41 are threaded tightly onto the threaded members 36, 37 which have previously been threaded tightly into the holes of wall members 11, 13. As the nuts 40, 41 are tightened, they force cone members 38, 43 into the conical chaped interior of threaded members 36, 37. The longitudinal openings 39 in the cone members permit the narrow end of the cone members to be forced together thereby squeezing and holding the rods 30, 31 which pass through the entire locking means.

The bone replacement polymer is then poured into the mold and the lid member 18 securely fastened over the open side. The through holes in the lid member 18 and the wall member 14 permit the elimination of air and excess polymer in cases where, e.g., the plates 26, 27 are released through the locking means and moved more closely together or the polymer is of a type which expands as it cures.

The mold can now be cured at room temperature or placed in a vacuum oven to hasten curing. Once cured, the bone replacement is removed, this process considerably eased by the presence of the panels 15, 16, 17, 19, 28, 29 of polytetraflouroethylene or a similar "nonstick" polymer.

The invention as thus described provides the surgeon and researchers with the ability to fabricate an almost infinite number of different size bone replacements or implants for use in humans and animals using a single mold.

Thus only one mold rather than many have to be built to support a laboratory. The sturdy construction of the mold and the locking means employed therewith permit the mold to withstand the pressures developed in the fabrication process without breaking or the interior dimensions changing. Furthermore, the mold can be sterilized by any of several commonly used methods. Finally, the interior panels of polytetrafluoroethylene permit easy removal of the cured bone replacement.

This mold is to Applicants' knowledge unique in the medical field. Its unique features will be a tremendous asset to researchers experimenting with polymer bone replacements.

We claim:

1. An adjustable mold comprising:
   (a) five wall members rigidly attached to each other to form a container structure being open on one side, said wall member opposite said open side having a plurality of through holes;
   (b) a lid member having a plurality of through holes, said lid member being adapted to fit sealing over said open side of said container structure;
   (c) means for releasably attaching said lid member to said container structure;

(d) at least one plate which is movable transversely between a nonintersecting pair of said wall members said plate sealingly contacting said pair of wall members and said wall member which is opposite said open side of said container structure;

(e) a rod attached to the side of said plate opposite the side in contact with a composition placed in said adjustable mold, said rod extending through a hole in one of said wall members, which is parallel with said plate, to the exterior of said adjustable mold;

(f) a hollow threaded member with a conical interior, which is in threaded engagement with said hole in said wall member through which said rod extends, said rod thereby also extending through said threaded member;

(g) a hollow cone member slidably received onto said rod and into the conical interior of said hollow threaded member, said cone member having longitudinal openings around the circumference and open to a narrow end of the cone member, thereby permitting the narrow end of said cone member to be tightly compressed around said rod when said cone member is forced into the conical interior of said hollow threaded member; and (h) an interiorly threaded nut which is closed at one end except for a hole having about the same diameter as that of said rod which permits said rod to extend therethrough and which when slid onto said rod and is threadably engaged with said threaded member forcing said cone member into said threaded member thereby compressing said cone member tightly around said rod thereby preventing movement thereof.

2. The adjustable mold as recited in claim 1, further comprising polytetrafluoroethylene polymer panels attached to the interior surfaces of said wall members, said lid member, and said plate.

* * * * *